Sept. 1, 1953 D. W. ULERY Plant Pat. 1,214
AFRICAN VIOLET PLANT
Filed Oct. 31, 1952
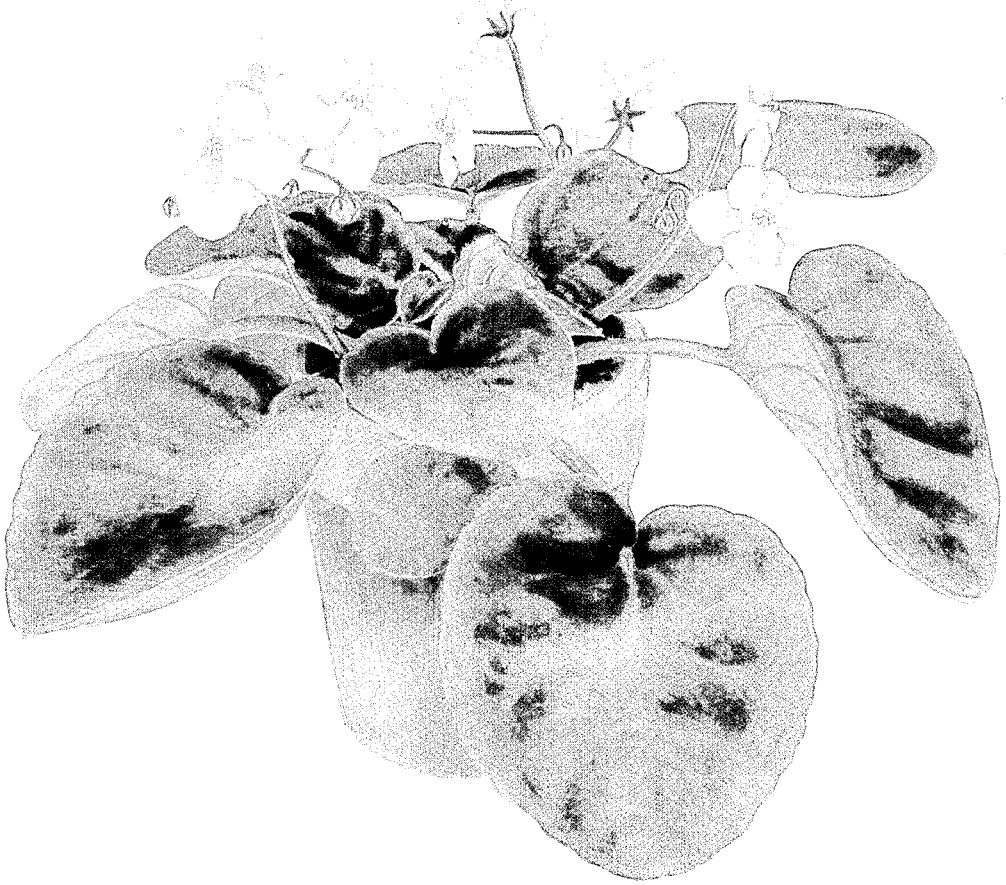
*INVENTOR.*
DALE W. ULERY
*BY* Toulmin & Toulmin
ATTORNEYS Patented Sept. 1, 1953

UNITED STATES PATENT OFFICE 1,214

AFRICAN VIOLET PLANT

Dale W. Ulery, Springfield, Ohio, assignor to Ulery Greenhouses, Springfield, Ohio, a partnership Application October 31, 1952, Serial No. 318,135

1 Claim. (Cl. 47—60)

The present discovery relates to a new and distant variety of African violet plant, a hybrid, resulting from the cross pollination of varieties derived from the cross pollination of Pink Beauty (Plant Patent No. 514) and the well known blue lavender Neptune (unpatented).

The new variety has been asexually reproduced by cuttings and its characteristics appear to be permanently fixed. There are presently over 600 plants in existence in a greenhouse at Springfield, Ohio, where the plant was originally produced.

The novel characteristics of this new variety reside particularly in the distinctively larger sizes of the leaves and flowers. The leaf which is of a good uniform green coloration attains at full growth a length and width of up to 4 inches, the length and width of the leaves being substantially equal. The flowers at full bloom attain a dimension of 1¾ x 1¾ inches which is greater than that normally occurring in this plant classification.

The accompanying illustration shows in full color a cluster of typical blossoms and leaves.

The predominant large green, substantially heart-shaped leaves set off the profusion of flat, disc-like flowers; these blossoms have a clear pink tint and from the center of each flower there protrudes the conspicuous yellow stamens. The foliage of the plant is compact with each leaf outstanding because of its size and coloration.

This new plant grows vigorously and thrives as a house plant, for dish gardens or pot plants.

The following is a detailed description of the new variety:

*Flower*

Blooming habit: Recurrent.
Size: 1¾ inches.
Form: Corolla is wide-campanulate.
Borne: Cymose inflorescence—1 to 8 flowers.
Shape: Elliptic but not equal.
Texture: Crystalline.
Stems: Sturdy and erect.
Petalage: 5.
Affected by wet or hot weather: No, except extremes.
Persistence: (Hang on and dry.) Bloom lasts about 2 weeks and then dries and drops off.
Lasting qualities: Very good.

*Plant*

Form: Rosette.
Foliage:
*Quantity.*—Abundant.

*Color.*—Under side of leaves silver toned; upper side of leaves dark green.
*Size of leaf.*—Up to 4 inches long and 4 inches wide—under average greenhouse conditions.
*Shape.*—Smooth edged, cordage.
*Texture.*—Pubescent; upper surface uniformly covered with short white hairs; lower surface glossy and ribbed.
*Petiole.*—Very sturdy, 3 inches long, ⅕ inch in diameter with nearly round section.

*Bud*

Size: ⅓ to ¼ inch.
Form: Gamosepalous—whitish green.
Sepals: Usually 5, pointed.
Calyx: Size ¼ inch; 5 lobed.
Genital organs:
*Stamens.*—Length—short; number—2, arched toward each.
*Anthers.*—Color—bright yellow.
*Arrangement.*—Side by side in abutting bilobate pairs.
*Color.*—Yellow.
*Pistil.*—Number—1; length—short.
*Stigma.*—Pink.

The color designations according to "A Dictionary of Color by Maerz and Paul," are as follows:

| | Plate | Letter | No. |
|---|---|---|---|
| Blossom: | | | |
| Main body of flower | 41 | F | 4 |
| Darker section at center | 41 | J | 5 |
| Stamens | 9 | H | 1 |
| Leaf: | | | |
| Main body of leaf | 23 | C | 7 |
| Under side of leaf | 17 | C | 3 |
| Large veins on under side of leaf | 17 | C | 5 |

This new variety of a pink African violet is easily distinguished from other varieties by the unusual large size of the leaves and flowers.

I claim:

A new and ornamental variety of African violet plant, substantially as illustrated and described, characterized by its vigorous compact growth, sturdy petioles and its predominant large green leaves and large clear pink blossoms.

DALE W. ULERY.

No references cited.